(12) United States Patent
Fernandez et al.

(10) Patent No.: US 9,993,364 B2
(45) Date of Patent: Jun. 12, 2018

(54) OSTOMY BAG

(71) Applicant: 3 West C, LLC, Tyler, TX (US)

(72) Inventors: Luis Fernandez, Tyler, TX (US);
James E. Deaton, Georgetown, TX (US); Charles R. Gordon, Tyler, TX (US)

(73) Assignee: 3 West C, LLC, Tyler, TX (US)

( * ) Notice: Subject to any disclaimer, the term of this patent is extended or adjusted under 35 U.S.C. 154(b) by 427 days.

(21) Appl. No.: 14/731,099

(22) Filed: Jun. 4, 2015

(65) Prior Publication Data
US 2015/0265455 A1 Sep. 24, 2015

Related U.S. Application Data

(63) Continuation-in-part of application No. 14/498,117, filed on Sep. 26, 2014.

(60) Provisional application No. 61/883,083, filed on Sep. 26, 2013.

(51) Int. Cl.
*A61F 5/445* (2006.01)
*A61F 5/448* (2006.01)

(52) U.S. Cl.
CPC ...... *A61F 5/448* (2013.01); *A61F 2005/4486* (2013.01)

(58) Field of Classification Search
CPC ...... A61F 2005/4483; A61F 2005/4486; A61F 2005/4495; A61F 5/445–5/449
USPC .......................................... 604/332–345, 355
See application file for complete search history.

(56) References Cited

U.S. PATENT DOCUMENTS

| | | | |
|---|---|---|---|
| 4,518,389 A | 5/1985 | Steer et al. | 604/339 |
| 4,553,967 A | 11/1985 | Ferguson et al. | 604/317 |
| 4,648,875 A | 3/1987 | Ferguson | 604/339 |
| 4,834,732 A | 5/1989 | Steer et al. | 604/342 |
| 4,929,245 A | 5/1990 | Holtermann et al. | 604/338 |
| 5,041,102 A | 8/1991 | Steer et al. | 604/338 |
| 5,180,377 A | 1/1993 | Holtermann | 604/342 |
| 5,250,042 A | 10/1993 | Torgalkar et al. | 604/333 |
| 5,322,526 A | 6/1994 | Nakamura et al. | 505/330 |
| 5,693,035 A | 12/1997 | Leise et al. | 604/333 |
| 5,961,501 A | 10/1999 | Cassidy et al. | 604/327 |
| 6,312,415 B1* | 11/2001 | Nielsen | A61F 5/443 604/327 |
| 6,409,710 B1 | 6/2002 | Holtermann | 604/342 |
| 6,451,883 B1* | 9/2002 | Chen | A61F 5/443 523/111 |
| 6,506,184 B1 | 1/2003 | Villefrance | 604/333 |
| 6,569,134 B1 | 5/2003 | Leise et al. | 604/332 |
| 6,712,800 B2 | 3/2004 | Kanbara | 604/333 |
| 6,773,420 B2 | 8/2004 | Kanbara | 604/333 |
| 7,789,866 B2 | 9/2010 | Poulsen et al. | 604/333 |
| 7,927,320 B2* | 4/2011 | Goldwasser | A61F 5/451 604/317 |
| 8,007,483 B2 | 8/2011 | Worsoee | 604/333 |
| 8,142,406 B2 | 3/2012 | Blum | 604/338 |
| 2003/0028161 A1* | 2/2003 | Carballo | A61F 5/453 604/349 |

(Continued)

OTHER PUBLICATIONS

International Search Report and Written Opinion issued in PCT/US2014/057725 dated Feb. 24, 2015.

*Primary Examiner* — Susan Su
(74) *Attorney, Agent, or Firm* — Norton Rose Fulbright US LLP

(57) ABSTRACT

A temporary stoma bag for receiving waste from a patient's stoma. The temporary stoma bag includes a bag and a sealing ring for temporary sealing against a stoma to facilitate changing of an ostomy bag or a stoma port for attaching an ostomy bag.

18 Claims, 7 Drawing Sheets

(56) References Cited

U.S. PATENT DOCUMENTS

| | | | |
|---|---|---|---|
| 2003/0060786 A1* | 3/2003 | Olsen | A61F 5/443 604/342 |
| 2004/0171999 A1* | 9/2004 | Andersen | A61F 5/4407 604/332 |
| 2006/0184145 A1* | 8/2006 | Ciok | A61F 5/443 604/338 |
| 2008/0071237 A1* | 3/2008 | Chen | A61F 5/451 604/352 |
| 2008/0262446 A1* | 10/2008 | Ryder | A61F 5/4407 604/317 |
| 2009/0234313 A1* | 9/2009 | Mullejeans | A61B 5/107 604/338 |
| 2010/0145292 A1* | 6/2010 | Mayer | A61F 5/443 604/337 |
| 2010/0168693 A1* | 7/2010 | Edvardsen | A61F 5/44 604/355 |
| 2011/0213322 A1 | 9/2011 | Cramer et al. | 604/344 |
| 2013/0060214 A1* | 3/2013 | Willoughby | A61F 5/445 604/338 |
| 2013/0138062 A1* | 5/2013 | Klein | A61F 5/443 604/336 |
| 2013/0253455 A1* | 9/2013 | Masters | A61F 5/445 604/332 |
| 2014/0148770 A1* | 5/2014 | Masters | A61F 5/4407 604/344 |
| 2015/0094675 A1* | 4/2015 | Kyvik | A61F 5/4407 604/337 |
| 2015/0190198 A1* | 7/2015 | Debel | A61F 5/445 604/344 |
| 2017/0157284 A1* | 6/2017 | Pearce | A61L 24/046 |

* cited by examiner

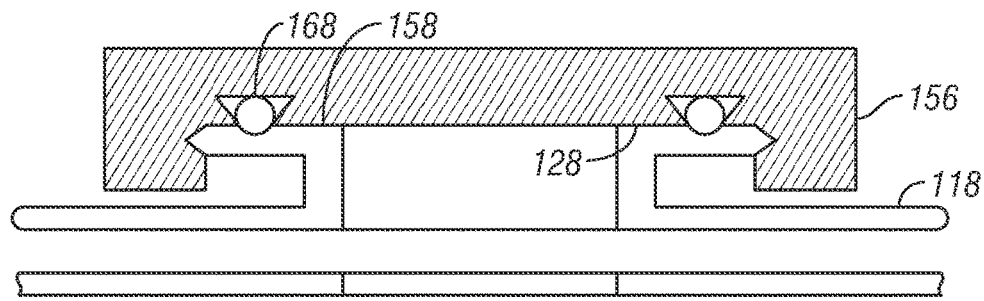
FIG. 6
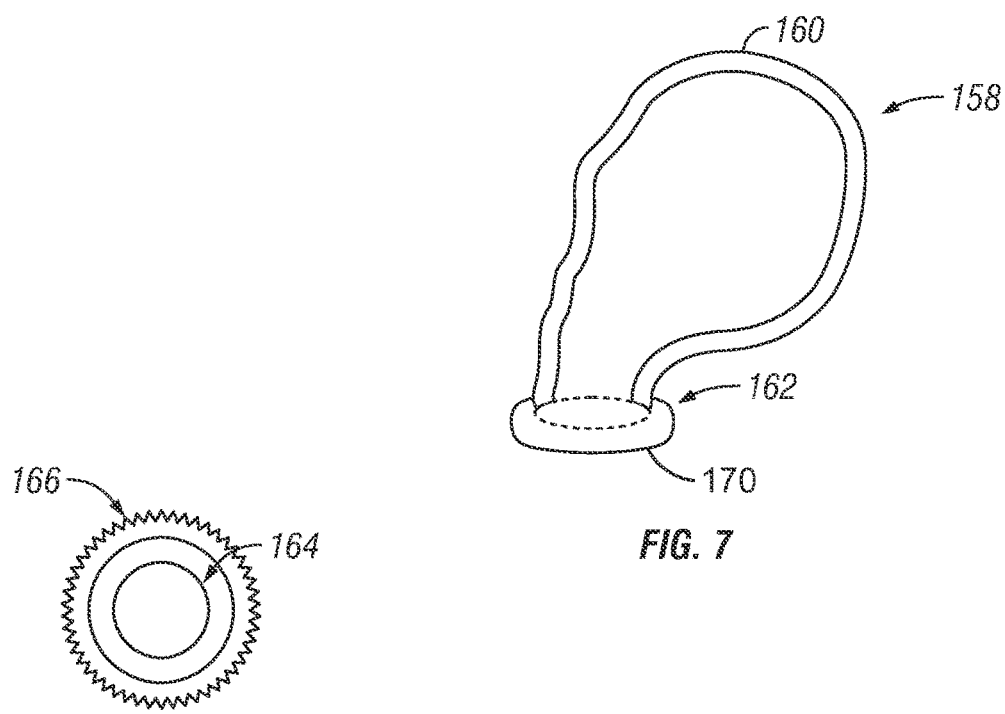
FIG. 7
FIG. 8

OSTOMY BAG

CROSS-REFERENCE TO RELATED APPLICATIONS

This application is a continuation-in-part of U.S. application Ser. No. 14/498,117, filed Sep. 26, 2014, which claims priority to U.S. Provisional Application No. 61/883,083, filed Sep. 26, 2013. The entire contents of these applications are specifically incorporated by reference herein without disclaimer.

BACKGROUND

1. Field of the Invention

The present invention relates to an ostomy bag for receiving waste from a patient's stoma.

2. Description of Related Art

An ostomy is a surgical procedure to create an opening (stoma) from an area inside the body to the outside. It is used to treat certain diseases of the digestive or urinary systems. It can be permanent or temporary. Three common ostomies are a colostomy, an ileostomy and an urostomy. In a colostomy, a stoma is formed in a patient's abdominal wall and the colon is attached to the stoma. In an ileostomy, a stoma is formed in a patient's abdominal wall and the bottom of the small intestine (i.e., the ileum) is attached to the stoma. In an urostomy, a stoma is formed in a patient's abdominal wall and a passage is created to allow urine to flow outside of the body.

Waste is discharged from the stoma, and the patient must wear an ostomy bag to collect the waste material. A wide variety of ostomy bags are in general use today. However, these bags suffer from various issues and there is a need for an improved ostomy bag.

SUMMARY

An improved ostomy bag is disclosed. In accordance with one embodiment, an ostomy bag comprises a bag member having an interior chamber for receiving waste from a patient's stoma and an opening for attachment to the patient's stoma. A finger probe is attached to the bag member, and the finger probe is configured to allow the patient to manipulate the stoma to clear blockages and the like. The finger probe may comprise a pouch attached to the bag member. The bag member may include a resealable opening for draining the bag.

The ostomy bag may further comprise a stoma port and a locking ring for sealing the opening in the bag member to the stoma port. The stoma port may be attached to the skin surrounding the stoma and has an opening therethrough and threads on an outer surface for engaging the locking ring. The stoma port may comprise a first mating surface and the locking ring may comprise a second mating surface for engaging the first mating surface to seal the bag to the stoma port. An o-ring may be disposed on one of the first and second mating surfaces. The locking ring may comprise at least one locking tab for engaging at least one locking recess disposed on the stoma port. The ostomy bag may be formed of an antimicrobial material, and the antimicrobial material may comprise silver. A locking cap for sealing the stoma port may be provided. A stoma bag for facilitating changing of the ostomy bag may be provided. The stoma bag may comprise a bag with a sealing ring for sealing the bag to the stoma.

In accordance with another exemplary embodiment, an ostomy bag for use with a stoma port attached to a patient's stoma is provided. The stoma port comprises a first mating surface with an aperture for passing waste from the patient's stoma therethrough. The ostomy bag comprises a bag having an interior chamber and an opening for receiving waste from a patient's stoma. A locking collar is disposed around the opening, and the locking collar forms a second mating surface configured for attachment to the first mating surface. The ostomy bag may further comprise an o-ring disposed in a recess on one of the first and second mating surfaces. The locking collar may comprise a threaded locking nut disposed around the opening for attachment to the stoma port. The locking nut may be fully engaged with a quarter turn. The locking nut may comprise at least one locking tab for engaging at least one locking recess disposed on the stoma port. The ostomy bag may further comprise a finger probe configured to allow the patient to manipulate the stoma to clear blockages. The finger probe may comprise a pouch attached to the bag member. The ostomy bag may comprise an antimicrobial material, and the antimicrobial material may comprise silver. A stoma bag for facilitating changing of the ostomy bag may be provided. The stoma bag may comprise a bag with a sealing ring for sealing the bag to the stoma.

In accordance with another exemplary embodiment, a temporary stoma bag for temporarily covering a stoma is provided. The temporary stoma bag includes a bag member having an interior chamber for receiving waste from a patient's stoma and an opening for surrounding a patient's stoma, wherein the volume of the bag member is only large enough for temporary usage, and a sealing ring for temporarily sealing the bag member to the patient's stoma. The temporary stoma bag may include a temporary adhesive on the sealing ring for temporarily attaching the sealing ring to a patient's skin surrounding a stoma. The temporary adhesive may be suitable for use less than one hour. The temporary stoma bag may include a drawstring for sealing the sealing ring against a stoma. The temporary stoma bag may include an elastic member for sealing the sealing ring against a stoma. The sealing ring may comprise a foam material. The volume of the bag member may be less than 300 cc, less than 200 cc, or less than 100 cc.

In accordance with another exemplary embodiment, a method of changing an ostomy bag receiving waste from a stoma comprises removing an ostomy bag from the stoma, placing a temporary stoma bag over the stoma, removing the temporary stoma bag after less than one hour, and placing an ostomy bag adapted for long-term usage over the stoma. The temporary stoma bag may comprise a bag member having an interior chamber for receiving waste from a patient's stoma and an opening for surrounding a patient's stoma, wherein the volume of the bag member is only large enough for temporary usage, and a sealing ring for temporarily sealing the bag member to the patient's stoma. The temporary stoma bag may include a temporary adhesive on the sealing ring for temporarily attaching the sealing ring to a patient's skin surrounding a stoma. The temporary adhesive may be suitable for use less than one hour. The temporary stoma bag may include a drawstring for sealing the sealing ring against a stoma. The temporary stoma bag may include an elastic member for sealing the sealing ring against a stoma. The sealing ring may comprise a foam material. The volume of the bag member may be less than 300 cc, less than 200 cc, or less than 100 cc.

The term "coupled" is defined as connected, although not necessarily directly. The terms "a" and "an" are defined as one or more unless this disclosure explicitly requires otherwise.

The terms "substantially," "approximately," and "about" are defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

A device, system, or component of either that is configured in a certain way is configured in at least that way, but it can also be configured in other ways than those specifically described.

Any embodiment of any of the systems and methods can consist of or consist essentially of—rather than comprise/include/contain/have—any of the described elements, features, and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF THE DRAWINGS

FIG. 6 is a section diagram of a cap for covering the stoma port of FIG. 3;

FIG. 7 is a side view of a stoma pouch for changing a colostomy bag;

FIG. 8 is a bottom view of the stoma pouch of FIG. 7;

DESCRIPTION OF ILLUSTRATIVE EMBODIMENTS

Figure 1:
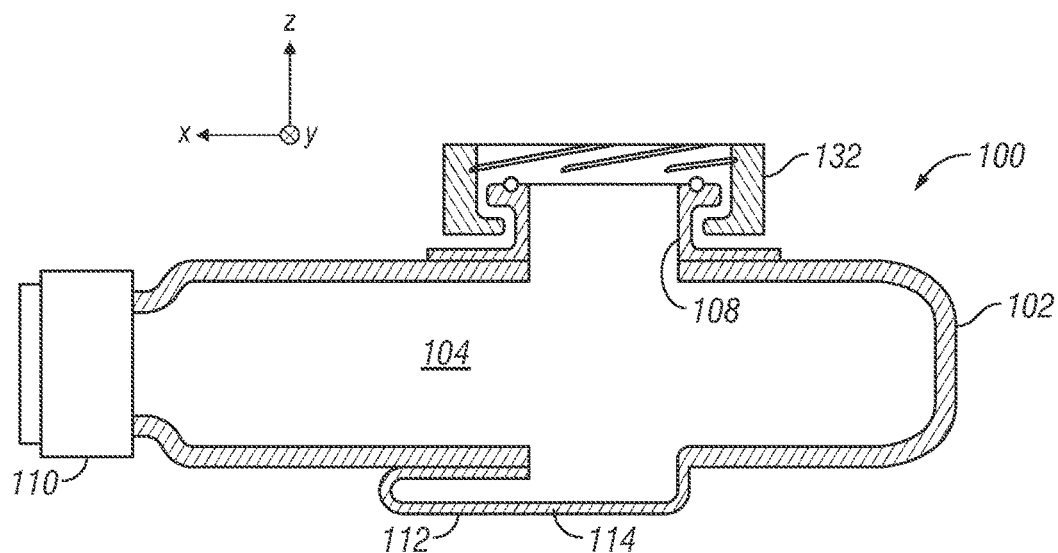
FIG. 1 is a sectional diagram of an ostomy bag in accordance with an embodiment of the present invention.
Figure 2:
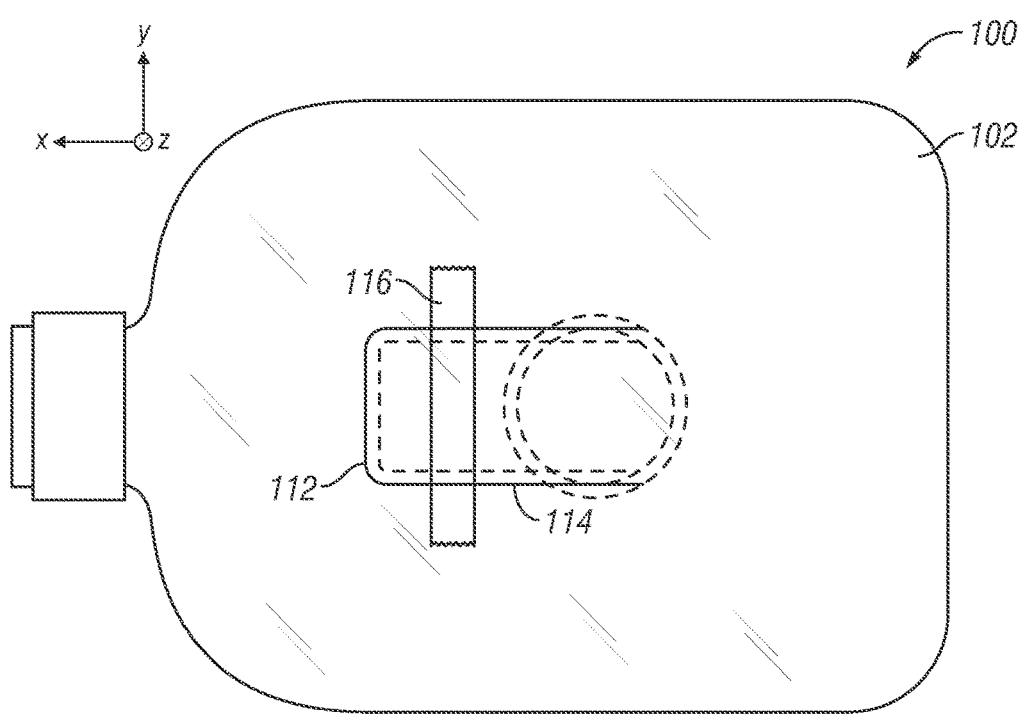
FIG. 2 is a plan view of the ostomy bag of FIG. 1.

In the following detailed description, reference is made to the accompanying drawings, in which are shown exemplary but non-limiting and non-exhaustive embodiments of the invention. These embodiments are described in sufficient detail to enable those having skill in the art to practice the invention, and it is understood that other embodiments may be used, and other changes may be made, without departing from the spirit or scope of the invention. The following detailed description is, therefore, not to be taken in a limiting sense, and the scope of the invention is defined only by the appended claims. In the accompanying drawings, like reference numerals refer to like parts throughout the various figures unless otherwise specified.

Referring to FIGS. 1-5, an ostomy bag 100 comprises a bag member 102 with an interior cavity 104 for receiving waste from a patient's stoma 106 through an opening 108. Bag member 102 may be formed of any liquid impermeable material, such as polyvinyl chloride, and may be constructed using any conventional manufacturing technique. In one embodiment, ostomy bag 100 is assembled using multiple pieces which are solvent welded together. Ostomy bag 100 may include an antimicrobial agent coated on or embedded in the material. In one embodiment, the antimicrobial agent is silver, such as silver nanoparticles, which have well known antimicrobial properties.

Ostomy bag 100 may be utilized with any type of ostomy. In certain embodiments, it is adapted for use with a colostomy or an ileostomy.

Ostomy bag 100 may be drainable or a disposable. A drainable ostomy bag includes a resealable opening 110 for draining ostomy bag 100. In one embodiment, resealable opening 110 comprises a tail which may be rolled up to seal the tail, which is then held shut with a closure strip. In another embodiment, resealable opening 110 comprises a threaded circular opening which may be covered with a threaded cap. Ostomy bag 100 may also include a vent (not illustrated) to allow gases to exit ostomy bag 100. In certain embodiments, the vent includes odor control agents, such as activated charcoal.

Ostomy bag 100 may include a finger probe or flap 112 to allow a user to manually manipulate a stoma. For example, if stoma 106 has a blockage, a user may insert his finger into finger probe 112 and remove the blockage without having to remove ostomy bag 100. In one embodiment, finger probe 112 comprises an elongate tube 114 which is sealed at one end and open to the interior of ostomy bag 100 at the other end. Finger probe 112 may be formed of the same material as the bag member of ostomy bag 100, or may be formed of thinner material to allow easier manipulation or stronger material to withstand repeated manipulation of the material without breakage. When not in use, finger probe 112 may be fastened to ostomy bag 100 using a closure strip 116. Closure strip 116 may comprise a refastenable material, such as hook and loop fasteners, or tape.

Ostomy bag 100 may be adapted to mate with a stoma port 118. Stoma port 118 is attached to the skin 120 surrounding stoma 106 using a gasket 122 with adhesive on both sides or the like. Stoma paste or similar material may be used to seal any openings which remain between the port and the patient's skin. Stoma port 118 may be left in place for an extended period of time, such as several days. This allows a patient to conveniently change ostomy bag 100 without the time-consuming process of preparing the surrounding skin 120 and adhering a new bag directly to the prepared skin 120.

In one embodiment, stoma port 118 comprises a skin facing surface member 124 with an opening 126 therethrough. Opening 126 in stoma port 118 is placed over patient's stoma 106 so that waste may flow from stoma 106 and through stoma port 118. In an embodiment, skin facing surface member 124 has a low profile and is formed of a plastic material which is comfortable for a patient to wear for an extended period of time.

A conduit 150 extends from skin facing surface member 124 to a mating surface 128. Conduit 150 conveys waste from opening 126 in stoma port 118 to mating surface 128. The conduit is typically short so that the patient does not have items protruding from the area of the stoma (e.g., the abdominal wall). In certain embodiments, mating surface 128 is flat. The outer circumference of the mating surface 128 forms threads 130 for connection with a locking retainer 132.

A flange member 134 is coupled to bag member 102 and has an opening for passing waste through flange member 134. A mating surface 136 on flange member 134 is configured to mate with mating surface 128 of stoma port 118. In certain embodiments, the mating surfaces 128, 136 are flat. However, they may also be configured in any other complementary shape. In certain embodiments, the mating surfaces 128, 136 further comprise an o-ring 138 arranged in a recess 140 in one of the mating surfaces. Recess 140 may comprise a dovetail slot in the face of mating surface 136 on flange member 134.

Figure 3:
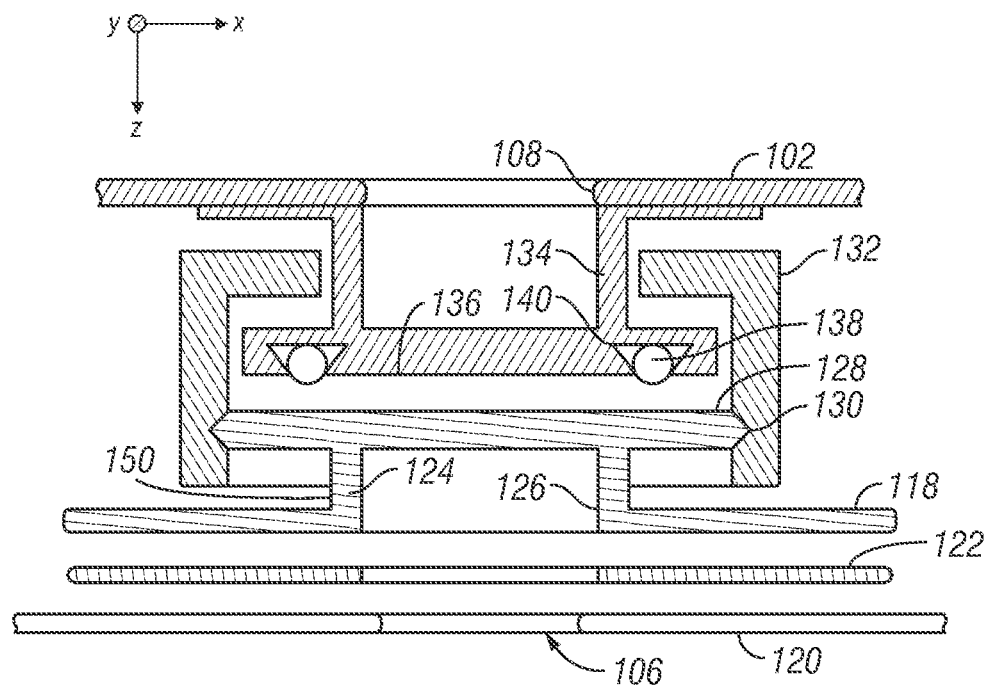
FIG. 3 is an enlarged section diagram of a stoma port and locking ring of the ostomy bag of FIG. 1.
Figure 4:
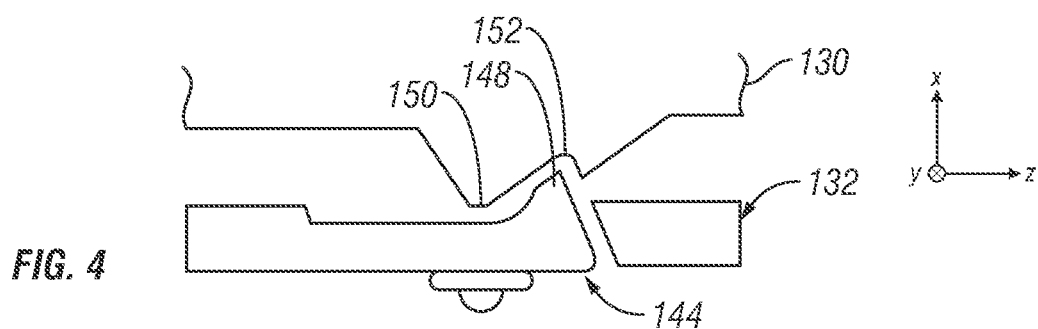
FIG. 4 is a sectional view of a quarter turn snap lock in accordance with an embodiment of FIG. 1.

A locking retainer 132 is provided to securely attach bag member 102 to stoma port 118. Locking retainer 132 may comprise a locking nut which surrounds flange member 134 on bag member 102. It should be noted that the gaps in FIG. 3 are exaggerated for clarity. Locking member 132 has internal threads which cooperate with external threads 130 on stoma port 118. Preferably, the threads are configured so that bag member 102 may be attached to and detached from stoma port 118 with a quarter turn.

Figure 5:
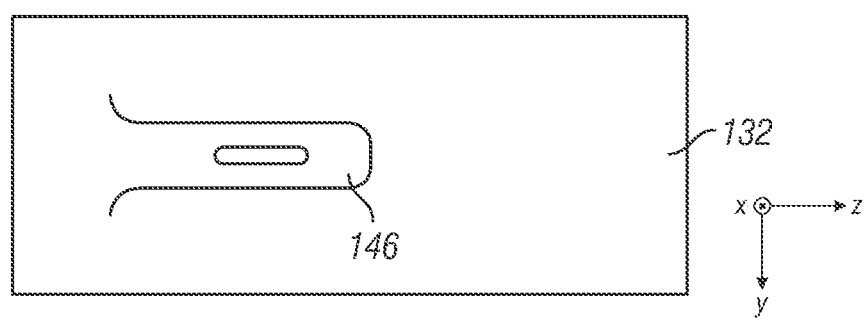
FIG. 5 is a side view of the quarter turn snap lock illustrated in FIG. 3.
Figure 9:
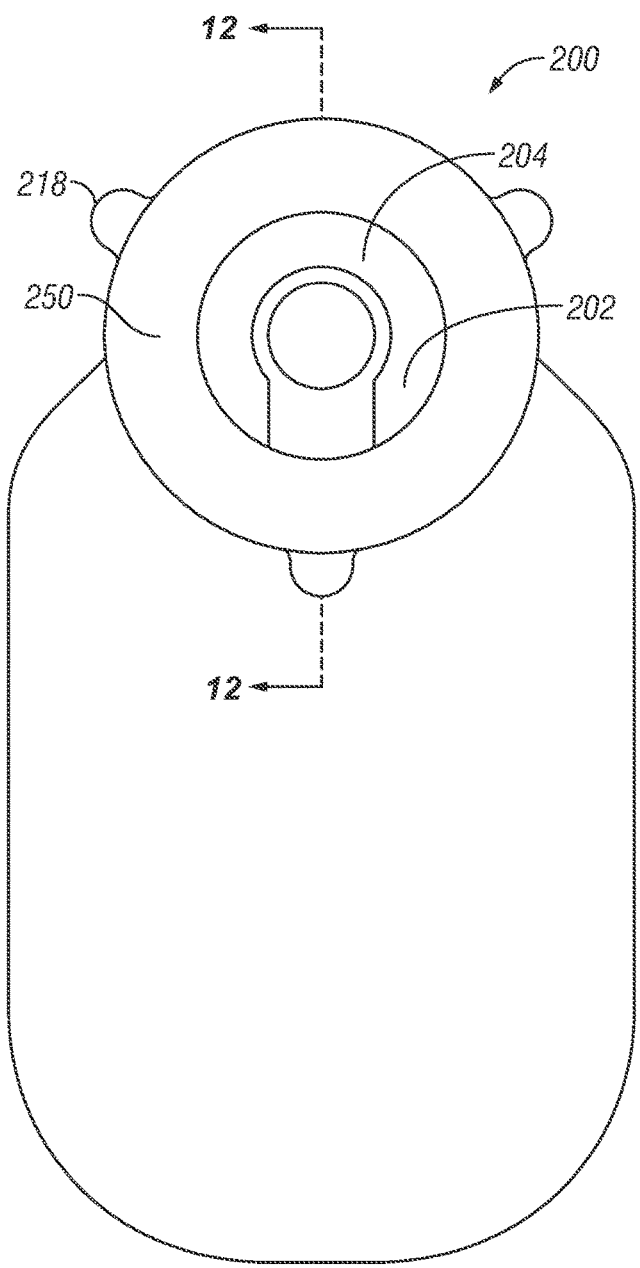
FIG. 9 is a plan view of an ostomy bag in accordance with an embodiment of the present invention.
Figure 10:
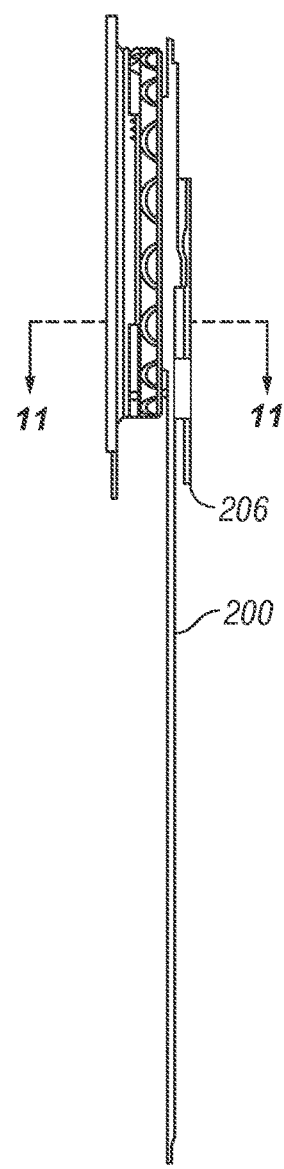
FIG. 10 is a side view of the ostomy bag of FIG. 9.
Figure 11:
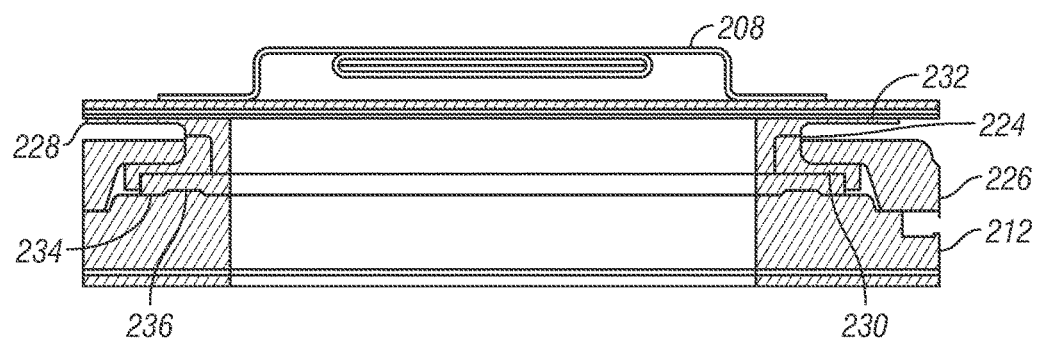
FIG. 11 is a sectional view taken along line 11-11 in FIG. 9.
Figure 12:
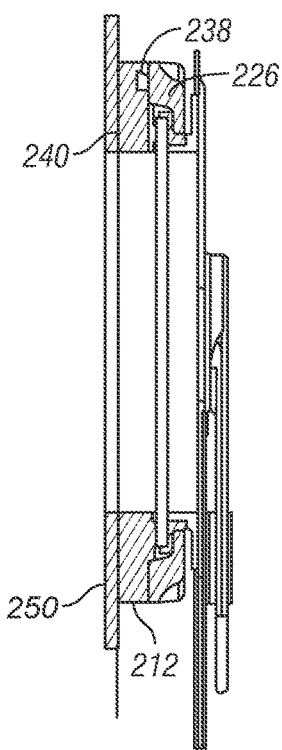
FIG. 12 is a sectional view taken along line 12-12 in FIG. 9.
Figure 13:
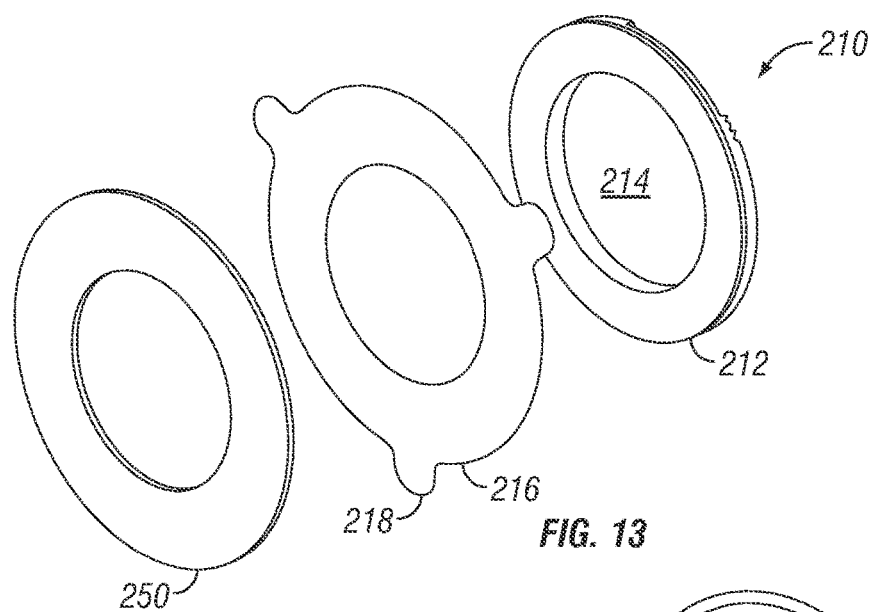
FIG. 13 is an exploded assembly view of a stoma port of the ostomy bag of FIG. 9.
Figure 14:
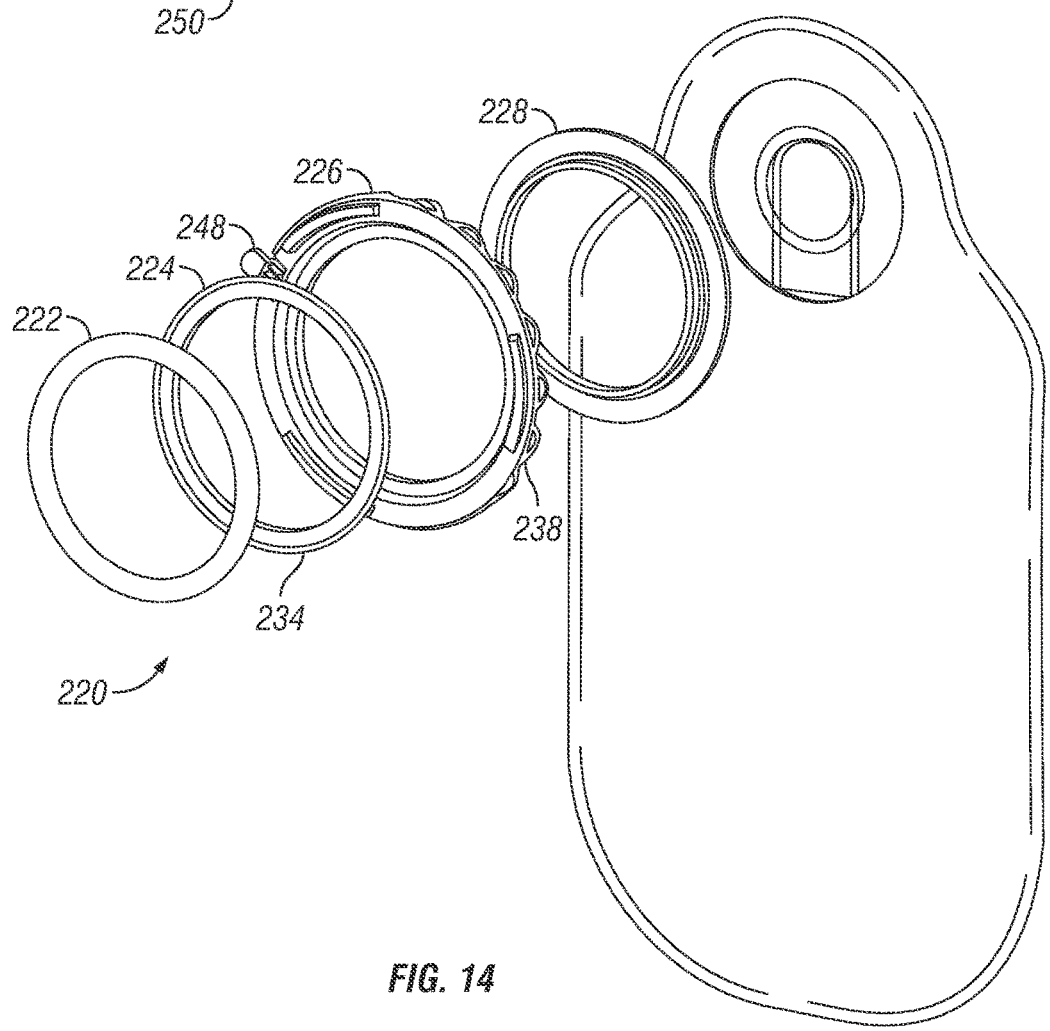
FIG. 14 is an exploded assembly view of the ostomy bag of FIG. 9.
Figure 15:
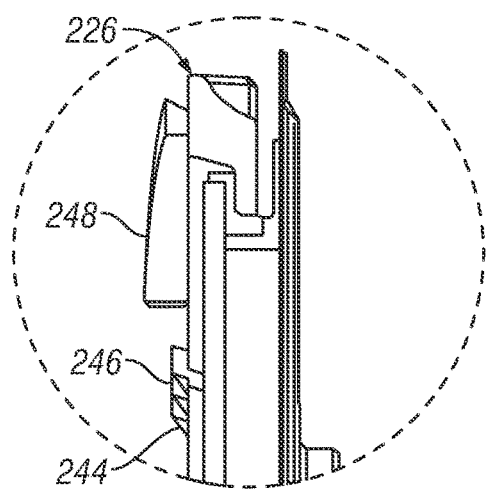
FIG. 15 is a detail view of the assembly of the ring assembly to the bag member of the ostomy bag of FIG. 9.
Figure 16:
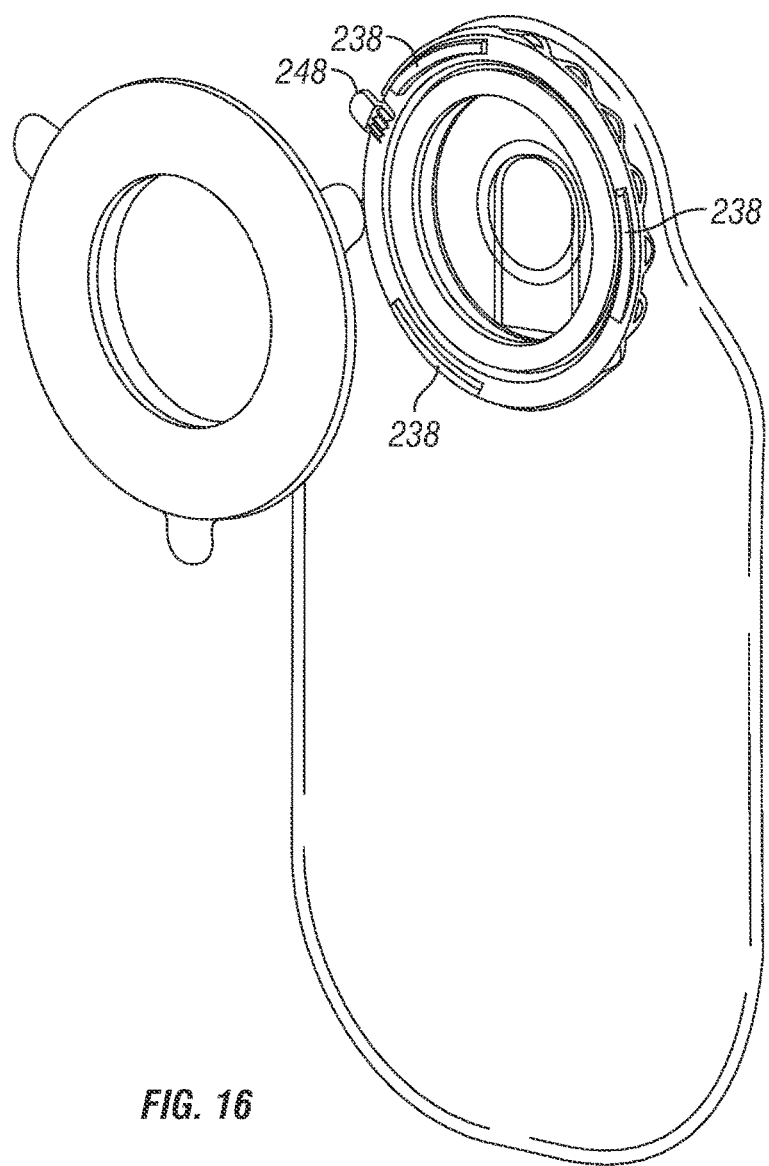
FIG. 16 is a perspective view of the stoma port and ostomy bag of FIG. 9.

Locking retainer 132 may include a snap lock 144 to securely fasten it to stoma port 118 and minimize the chances of inadvertently releasing bag member 102 from stoma port 118. As seen in FIGS. 5 and 6, the locking retainer 132 has a flexible tongue 146 with a protrusion 148. The threads on stoma port 118 contains a ramp 150 with a recess 152. When locking retainer 132 is rotated into position, protrusion 148 is guided by ramp 150 and snaps into recess 152 to provide a positive lock. In some embodiments, tongue 146 makes an audible click to provide feedback to the user. Snap lock 144 may be disengaged by pressing on the back side of flexible tongue 146, which levers protrusion 148 out of recess 152 and allows locking retainer 132 to be reversed and removed.

As seen in FIG. 6, a cap member 156 may be provided to facilitate changing of the colostomy bag. The patient is unable to control discharge of waste from stoma 106, and waste may leak from stoma 106 while the patient is changing ostomy bag 100. To prevent this leakage, a cap member 156 may be provided to place on stoma port 118 while changing the bag. Cap member 156 has a similar construction to locking retainer 132. In the illustration of FIG. 6, cap member 156 is tightened so that stoma port mating surface 128 and cap mating surface 158 are pressed against one another and o-ring 168 is compressed to form a tight seal. Cap member 156 may be fully engaged with a quarter turn lock, and may use a locking retainer as previously described.

As seen in FIGS. 7 and 8, a temporary stoma bag 158 may be provided to facilitate changing of the stoma port 118 or another appliance, such as a standard ostomy bag. As used in connection with this embodiment, "temporary" denotes a time period which is sufficient to allow changing of a stoma port or other appliance, but does not encompass longer-term usage. For example, "temporary" means a period of time less than an hour, a half-hour, fifteen minutes, or ten minutes. Temporary does not include long-term usage—that is, usage longer than one hour. Since a patient is unable to control discharge of waste from stoma 106, temporary stoma bag 158 may be placed over the stoma 106 while changing the stoma port 118 to capture and manage any waste discharged from the stoma 106. Temporary stoma bag 158 comprises a bag member 160 formed of a liquid impermeable material and a sealing ring 162 for sealing the bag member 160 to stoma 106. The volume of temporary stoma bag 158 is small compared to a standard ostomy bag, and is only suitable for temporary usage. For example, the volume of temporary stoma bag 158 could be between 100-300 cc. Sealing ring 162 contains an inner ring 164 of a soft, pliable material that may be pressed against stoma 106 to temporarily seal sealing ring 162 against stoma 106. One suitable material is a soft foam material. An adhesive material 170 may be provided on the bottom (i.e., skin-facing) surface of the sealing ring 162. The adhesive material 170 may be a low-tack adhesive material so that it can be easily removed from a patient's skin without damage and permit temporary fixation of the temporary stoma bag 158 to stoma 106. An adjustable layer 166 may be provided on the outside of the inner ring 164. Adjustable layer 166 provides tension to hold sealing ring 162 against stoma 106. Adjustable layer 166 may comprise an elastic material or a drawstring.

Referring to FIGS. 9-16, another embodiment of an ostomy bag 200 comprises a bag member 200 with an interior cavity 202 for receiving waste from a patient's stoma through an opening 204. Ostomy bag 200 may include a finger probe or flap 206 to allow a user to manually manipulate a stoma, as described above. A strap 208 may be provided to hold the finger probe in place when not in use.

Ostomy bag 200 may be adapted to mate with a stoma port 210. Stoma port 210 comprises a stoma port ring 212 with an opening 214 therethrough, a stoma port removal ring 216 coupled to stoma port ring 212, and an adhesive foam gasket 250. Stoma port removal ring 216 has outwardly extending tabs 218 to allow a user to grasp stoma port 210 to aid in holding in place during bag installation and removal. Opening 214 in stoma port 210 is placed over a patient's stoma and adhered to the patient's skin with adhesive gasket 250 so that waste may flow from the stoma and through stoma port 210. In an embodiment, stoma port 210 has a low profile and is formed of a plastic material which is comfortable for a patient to wear for an extended period of time.

Ostomy bag 200 has a ring assembly 220 that mates with stoma port 210. Ring assembly 220 comprises a gasket seal 222, and interface ring 224, a locking ring 226 and a bag ring 228. Bag ring 228 is coupled to the bag member 202. Locking ring 226 is placed over the bag ring 228, and interface ring 226 is coupled to bag ring 228 to capture locking ring 226 between the flanges 230, 232 at the edges of interface ring 224 and bag ring 228.

Interface ring 224 and stoma port ring 212 may have opposed surfaces 234, 236. Gasket 222 may be disposed between locking 226 and interface ring 224 to provide a substantially fluid tight connection. Locking ring 226 may have one or more face threads 238 which correspond with complementary threads 240 in stoma port 210 (see FIG. 12). In the exemplary embodiment shown, face threads 138 are dovetail shaped, and complementary threads 240 have an opening portion and a mating portion 242. The face threads 138 are inserted into the opening and then rotated into the mating portion 242 to couple interface ring 224 to stoma port ring 212. This face thread assembly helps produce a lower profile, which increases patient comfort. A locking assembly 242 may be provided to hold interface ring 224 in place with respect to stoma port ring 212. In one embodiment, locking assembly 242 comprises a pair of mating sawtooth profiles 244, 246. Sawtooth profiles 244, 246 may be disengaged from one another by manipulating locking tab 248 to allow removal of ostomy bag 200.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

What is claimed is:

1. A temporary stoma bag for temporarily covering a stoma comprising:
    a bag member having an interior chamber for receiving waste from a patient's stoma and an opening for surrounding the patient's stoma, wherein a volume of the bag member is only large enough for temporary usage;
    a sealing ring for temporarily sealing the bag member to the patient's stoma; and
    a drawstring for sealing the sealing ring against the patient's stoma.

2. The temporary stoma bag of claim 1, further comprising a temporary adhesive on the sealing ring for temporarily attaching the sealing ring to a patient's skin surrounding a stoma.

3. The temporary stoma bag of claim 2, wherein the temporary adhesive is only suitable for use for less than one hour.

4. The temporary stoma bag of claim 1, further comprising an elastic member for sealing the sealing ring against a stoma.

5. The temporary stoma bag of claim 1, wherein the sealing ring comprises a foam material.

6. The temporary stoma bag of claim 1, wherein the volume of the bag member is less than 300 cc.

7. The temporary stoma bag of claim 1, wherein the volume of the bag member is less than 200 cc.

8. The temporary stoma bag of claim 1, wherein the volume of the bag member is less than 100 cc.

9. A method of changing an ostomy bag receiving waste from a stoma, comprising,
    removing an ostomy bag from the stoma,
    placing a temporary stoma bag over the stoma;
    removing the temporary stoma bag after less than one hour; and
    placing an ostomy bag adapted for long-term usage over the stoma.

10. The method of claim 9, wherein the temporary stoma bag comprises:
    a bag member having an interior chamber for receiving waste from the stoma and an opening for surrounding the stoma, wherein a volume of the bag member is only large enough for temporary usage; and
    a sealing ring for temporarily sealing the bag member to the stoma.

11. The method of claim 10, wherein the temporary stoma bag further comprises a temporary adhesive on the sealing ring for temporarily attaching the sealing ring to skin surrounding the stoma.

12. The method of claim 11, wherein the temporary adhesive is only suitable for use for less than one hour.

13. The method of claim 10, wherein the temporary stoma bag further comprises a drawstring for sealing the sealing ring against the stoma.

14. The method of claim 10, wherein the temporary stoma bag further comprises an elastic member for sealing the sealing ring against the stoma.

15. The method of claim 10, wherein the sealing ring comprises a foam material.

16. The method of claim 10, wherein the volume of the bag member is less than 300 cc.

17. The method of claim 10, wherein the volume of the bag member is less than 200 cc.

18. The method of claim 10, wherein the volume of the bag member is less than 100 cc.

* * * * *